United States Patent [19]

Morrow

[11] Patent Number: 4,465,683

[45] Date of Patent: * Aug. 14, 1984

[54] ANTI-PSYCHOTIC AGENTS

[75] Inventor: Duane F. Morrow, Evansville, Ind.

[73] Assignee: Mead Johnson & Company, Evansville, Ind.

[*] Notice: The portion of the term of this patent subsequent to Mar. 3, 1998 has been disclaimed.

[21] Appl. No.: 75,580

[22] Filed: Sep. 14, 1979

[51] Int. Cl.$^3$ .................. A61K 31/495; C07D 401/14
[52] U.S. Cl. ..................................... 424/250; 544/362
[58] Field of Search ........................ 424/250; 544/362

[56] References Cited

U.S. PATENT DOCUMENTS 3,381,009  4/1968  Palazzo et al. ...................... 544/362
4,254,124  3/1981  Morrow .............................. 544/362

FOREIGN PATENT DOCUMENTS 21074  8/1966  Italy .................................... 544/362

OTHER PUBLICATIONS

Silvestrini et al., Int. J. Neuropharmacol. 7, 587–599, (1968).
Fabre et al., Current Therapeutic Research 25, (6), 827–834, (1979).
Galvan et al., Current Therapeutic Research 15, (108), 776–880, (1973, Oct. Supplement).
Ban et al., Current Therapeutic Research 15, (8), 540–551, (1973).

Primary Examiner—Donald G. Daus
Assistant Examiner—S. A. Gibson
Attorney, Agent, or Firm—Robert H. Uloth; Robert E. Carnahan

[57] ABSTRACT

2-[4-[4-Arylpiperazin-1-yl]butyl]-1,2,4-triazolo[4,3-a]pyridin-3(2H)-ones are anti-psychotic agents.

5 Claims, No Drawings

ANTI-PSYCHOTIC AGENTS

FIELD OF THE INVENTION

This invention is concerned with heterocyclic carbon compounds of the piperazine series having an additional pyridine ring which is part of a bicyclo ring system (Class 544, Subclass 362). It is also concerned with drug, bio-affecting, and body-treating processes employing these compounds (Class 424, Subclass 250).

DESCRIPTION OF THE PRIOR ART

U.S. Pat. No. 3,381,009 patented Apr. 30, 1968 refers to 1,2,4-triazolo[4,3-a]pyridines which are lower homologs of the compounds of the present invention. The preferred compound of this group of prior art substances is 2-[3-[4-(3-chlorophenyl)-1-piperazinyl]-propyl]-1,2,4-triazolo[4,3-a]pyridin-3(2H)-one which is known by the name trazodone and has also been referred to as AF 1161. Pharmacological data summarized in the foregoing patent reveals that trazodone exhibits tranquilizing action, hypotensive action, and analgesic action in various animal tests. The data resemble that of the major tranquilizers or anti-psychotic agents such as chlorpromazine more than the minor tranquilizers or anxiolytic agents such as meprobamate and diazepoxide.

The pharmacological properties of trazodone have been described in more detail by Silvestrini, et al. in International Journal of Neuropharmacology, 7, 587–599 (1968). In clinical use the compound has proven to be an antidepressant equivalent in effectiveness to imipramine but with fewer side effects (Fabre, et al., Current Therapeutic Research, 25, 827–834 (1979)). Its anti-psychotic action in schizophrenic patients is, however, minimal (Galvan, et al., Current Therapeutic Research, 15, 776–780 (1973, Oct. Supplement)) except that an improvement in depressive symptoms exhibited by schizophrenics is effected (Ban, et al., Current Therapeutic Research, 15, 540–551 (1973))

SUMMARY OF THE INVENTION

The compounds with which the present invention is concerned are triazolo[4,3-a]pyridin-3(2H)-ones having the following structural formula

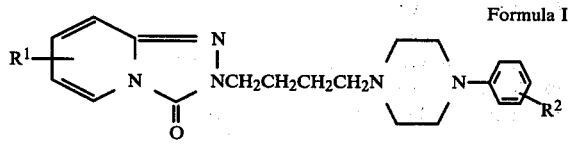

Formula I wherein $R^1$ is hydrogen or lower alkyl having 1 to 4 carbon atoms located in the 5, 6, 7, or 8 position of the triazolo[4,3-a]pyridin-3(2H)-one ring. $R^2$ is hydrogen, lower alkyl having 1 to 4 carbon atoms, lower alkoxy having 1 to 4 carbon atoms, halogen, or trifluoromethyl. $R^2$ is located in any of the 2, 3, or 4 positions of phenyl ring. The invention includes the pharmaceutically acceptable acid addition salts of the foregoing substances and their use in the treatment of psychotic conditions including schizophrenia.

The pharmaceutically acceptable acid addition salts are those in which the anion does not contribute significantly to the toxicity or pharmacological activity of the salt and, as such, they are the pharmacological equivalents of the bases of Formulas I. They are preferred for medical usage. In some instances, they have physical properties which make them more desirable for pharmaceutical formulation purposes such as solubility, lack of hygroscopicity, compressibility with respect to tablet formation and compatibility with other ingredients with which the substance may be used for pharmaceutical purposes. The salts are made by reaction of the base of Formula I with the selected acid preferably by contact in solution. They may also be made by metathesis or treatment with an ion exchange resin under conditions in which the anion of one salt of the substance of the Formula I is replaced by the anion of another under conditions which allow for separation of the undesired species such as by precipitation from solution or extraction into a solvent, or elution from or retention on an ion exchange resin. Pharmaceutically acceptable acids for the purposes of salt formation of the substances of Formula I include hydrochloric, hydrobromic, hydroiodic, citric, acetic, benzoic, phosphoric, nitric, mucic, isethionic, glucosaccharic, palmitic, heptanoic, and others.

The toxicities and physical properties of the present substances are similar to those of trazodone and, accordingly, they may be safely administered by the oral or parenteral routes in the treatment of psychotic patients in doses of similar size and type to those of trazodone employed in the treatment of patients suffering from depression. The dosage of the present substances for adult humans having psychotic disorders falls within the range of about 150 to 600 mg. per day orally or parenterally in a single or divided units. In animal tests reflecting anti-psychotic action the compounds are about two- to four-fold as active as chlorpromazine which also serves as a guide to dosage size.

DETAILED DESCRIPTION OF THE INVENTION

The measurement of conditioned avoidance response (CAR) in rats according to the shuttle box technique (Albert, et al., Pharmacologist, 4, 152 (1962)) is a commonly used laboratory test to measure anti-psychotic action. The apparatus employed is a box having a six-inch barrier separating two equal compartments. The floor of the left side of the box contains an electrified grid by means of which an intermittent shock is administered. The other side is not electrified. Rats are trained by placing them individually in the electrified compartment of the box and administering a foot shock which causes the rat to jump the barrier to the non-electrified side. After a brief training period, rats without fail will jump the barrier within 30 seconds of being placed in the left side of the box without administration of a foot shock. The test drug is then administered in various doses to different groups of rats and the effect of the treatment in terms of the number of rats which fail to jump the barrier before receiving a foot shock is measured. That dose of test drug which will reduce the number of conditioned animals jumping the barrier before receiving a foot shock by one-half is referred to as the $CAR-ED_{50}$. The following is a tabulation of the $CAR-ED_{50}$ values for chlorpromazine, a recognized anti-psychotic drug, trazodone, and several compounds of the present invention each, when administered by the oral route.

| ORAL CAR-ED$_{50}$ (mg/kg) | |
| --- | --- |
| Chlorpromazine | 38.7 |
| Trazodone | 45.4 |
| Formula I, R$^1$ = H, R$^2$ = 3-Cl | 9.0 |
| Formula I, R$^1$ = H, R$^2$ = 3-CF$_3$ | 11.4 |
| Formula I, R$^1$ = H, R$^2$ = 2-CH$_3$O | 18.4 |

Other laboratory animal tests reflective of anit-psychotic, anti-depressant, and analgesic activity have afforded the following comparisons. The compound of Formula I lacks antidepressant action which is the chief established clinical utility of trazodone. The present compounds are anti-psychotic agents to be distinguished from trazodone which is an antidepressant.

|  | Formula I R$^1$ = H, R$^2$ = 3-Cl | Trazodone |
| --- | --- | --- |
| Prevention of pernicious preening in mice (anti-psychotic or analgetic)[1] | ED$_{50}$ 8 mg/kg (p.o.) | ED$_{50}$ 43 mg/kg (p.o.) |
| Prevention of reserpine ptosis in mice (anti-depressant)[2] | inactive at 15.7 mg/kg (p.o.) | ED$_{50}$ 36 mg/kg (p.o.) |
| Reduction of phenyl-quinone writhing in mice (analgesic)[3] | ED$_{50}$ 23 mg/kg (p.o.) | ED$_{50}$ 21.8 mg/kg (p.o.) |

[1] Wilfon, et al., Fed. Proc. 19, 21 (1960).
[2] Niemegeers, Industrial Pharmacology, Vol. 2 - Antidepressants, Ed. by S. Fielding and H. Lal, pp. 73-98, Futura, New York, N.Y., (1975).
[3] Hendershot, et al., J. Pharmacol. Exptl. Therap. 125, 237 (1959).

The compounds of the present invention are made according to the reactions shown in the following scheme in which R$^1$ and R$^2$ have the same meaning as indicated above, and X and X' are independently selected from the group consisting of chlorine, bromine, and iodine. Preferably at least one of X and X' is bromine or iodine.

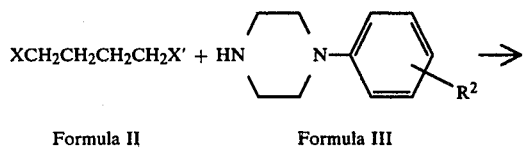

Formula II    Formula III

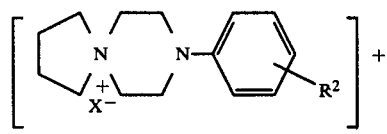

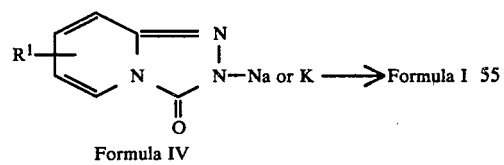

Formula IV

The process involves bringing together the starting materials of Formulas II, III, and IV in substantially equal molecular quantities in a liquid reaction medium which is inert under the reaction conditions and in the presence of a strong base such as an alkali metal oxide, hydroxide, amide, alcoholate, or carbonate. Preferably a liquid reaction medium is selected which has a boiling point in the range of about 80° to 150° C. and the reaction is carried out at the reflux temperature of the liquid medium. Suitable reaction inert liquid media include the liquid hydrocarbons, hydrocarbon nitriles and hydrocarbon ethers such as xylene, acetonitrile, and dibutylether. Preferably the reaction is carried out in stepwise fashion with the reactants of Formula II and Formula III first being heated within the above range in the presence of the base in the liquid reaction medium for a period of from 2 to 24 hrs. with the formation of the intermediate 8-substituted 8-aza-5-azoniaspiro[4,5]decane salt shown in brackets. This material is not isolated, but is allowed to react with the intermediate of Formula IV at the reaction temperature by the addition thereof to the reaction mixture in the second stage of the process. The reactant of Formula IV may be added without cooling to the reaction mixture and heating is continued for a period of from 2 to 72 hrs.

The reactants of Formulas II and III are articles of commerce or can be prepared by known methods. The triazolopyridines of Formula IV have been described in the literature and can be conveniently prepared by the reaction of 2-chloro-6-R$^1$ pyridine with semicarbazide. The sodium and potassium salts thereof are formed by dissolving the heterocycle in warm aqueous sodium hydroxide or potassium hydroxide and allowing the salt to crystallize from the solution on cooling.

DESCRIPTION OF SPECIFIC EMBODIMENTS

In the following procedures temperatures are expressed in degrees Centrigrade. Melting points are corrected values according to the USP method where indicated (corr.). The nuclear magnetic resonsance (NMR) spectral characteristics refer to chemical shifts down field (δ) expressed as parts per million (ppm) versus tetramethylsilane as referenced standard. The relative area reported for the various shifts corresponds to the number of hydrogen atoms in the individual substituent and the nature of the shift as to multiplicity is reported as broad singlet (bs), singlet (s), multiplet (m), doublet (d), triplet (t), or quadruplet (q) with coupling constant reported where appropriate. The format is NMR (solvent): δ(relative area, multiplicity, J value, and, in some instances, indicated structural characteristics). Abbreviations employed are EtOH (ethanol), Et$_2$O (ethyl ether), DMSO-d$_6$ (deuterodimethylsulfoxide), IR (infrared), KBr (potassium bromide), and d (decomposition). Others have well established meanings. The infrared spectra described include only absorption wavelengths (cm$^{-1}$) having functional group identification value. Unless indicated otherwise, KBr was employed as diluent for IR spectral determinations.

PROCEDURE 1

1,2,4-Triazolo[4,3-a]pyridin-3(2H)-one

A mixture of 50 g. (0.44 mole) of 2-chloropyridine and 98.22 g. (0.88 mole) of semicarbazide hydrocloride in 150 ml. of 2-ethoxyethanol was heated to reflux and then treated with a solution of 1 ml. of concentrated sulfuric acid (36 N) in 5 ml. of 2-ethoxyethanol. The resulting solution was refluxed for 18 hr., cooled to about 60°, and treated with 150 ml. of water. The mixture was stirred, cooled to 0°, and kept 0.5 hr. and the solid was collected on a filter. The solid was washed well with water and dried under reduced pressure, to give 35.0 g. (59%) of product, m.p. 230°-231°, which was sufficiently pure to be used for the next step.

Anal. Found: C, 52.96; H, 3.75; N, 30.94.

PROCEDURE 2.

5-Methyl-1,2,4-triazolo[4,3-a]pyridin-3(2H)-one

The method of Procedure 1 was repeated using 2-chloro-6-methylpyridine as starting material. The product was obtained in 33% yield, m.p. 182°–183°.

Anal. Found: C, 56.42; H, 4.80; N, 28.30.

PROCEDURE 3

Sodium 1,2,4-Triazolo[4,3-a]pyridin-3(2H)-one

The triazole from Procedure 1 (41.2 g., 0.31 mole) was dissolved in a solution of 12.19 g. (0.31 mole) of NaOH in 230 ml. of water at 80°. The solution was then chilled at 5° and left overnight. The resulting precipitate was collected on a filter and dried under reduced pressure, to afford 360 g. (75%) of light yellow salt, m.p. 320°. Concentration of the mother liquors afforded an additional 8.3 g. (17%) of salt. The triazole of Procedure 2 was converted to the sodium salt in the same fashion.

PROCEDURE 4

2-[4-[4-(3-Chlorophenyl)piperazin-1-yl]butyl]-1,2,4-triazolo[4,3-a]pyridin-3-(2H)-one A mixture of 8.0 g. (0.0343 mole) of 1-(3-chlorophenyl)piperazine hydrocloride, 5.88 g. (0.0343 mole) of 1-bromo-4-chlorobutane, 9.48 g. (0.9686 mole) of finely powdered potassium carbonate, and 200 ml. of dry xylene was refluxed for 22 hr. To this mixture there was then added 5.39 g. (0.0343 mole) of sodium 1,2,4-triazolo[4,3-a]pyridin-3(2H)-one, and the resulting suspension was refluxed an additional 72 hr. The mixture was then cooled, diluted with 200 ml. of chloroform, stirred for 15 min. and filtered. The clear filtrate was concentrated to an oil (9.8 g.) under reduced pressure. The residue was recrystallized from $ET_2O$—EtOH—$CHCl_3$ to afford 2.31 g. (43%) of the desired product, m.p. 122°–123°.

Anal. Found: C, 62.04; H, 6.18; N, 18.50.

NMR (DMSO-$d_6$): 1.85 (4,m), 2.56 (6,m), 3.21 (4,m), 4.10 (2,t, 7.0 Hz), 7.10 (7,m), 8.11 (1,m).

IR: 690, 750, 980, 1240, 1440, 1590, 1640, 1710, 2820, 2940, 3100 cm$^{-1}$.

PROCEDURE 5

2-[4-[4-[3-(Trifluoromethyl)phenyl]-1-piperazinyl]butyl]-1,2,4-triazolo[4,3-a]pyridin-3(2H)-one Hydrochloride 1-[3-Trifluoromethyl)phenyl]piperazine, 11.51 g. (0.05 mole) and 10.8 g. (0.05 mole) of 1,4-dibromobutane and 27.64 g. (0.2 moles) of potassium carbonate and 225 ml. of xylene was refluxed for 24 hrs. Sodium 1,2,4-triazolo-[4,3-a]pyridin-3-one, 7.85 g. (0.05 mole) was then added and the mixture was refluxed for an additional 80 hrs. The mixture was then allowed to cool to room temperature, diluted with 300 ml. of chloroform and filtered. The solvent was then evaporated from the filtrate in vacuo to yield an oily residue weighing 21.87 g. The oil was triturated with hexane to yield 16.33 g. of solid product. This material was recrystallized from acetonitrile yielding 14.09 g. of the product in free base form, m.p. 101°–103° (67.2%) which was converted to the hydrocloride salt by dissolving in 70 ml. of ethanol and treating with 9.7 ml. of 3.4 N ethanolic HCl, yield 14 g. This material was recrystallized from 200 ml. of isopropanol, yield 10.6 g. (46.3%), m.p. 191°–193° (corr.).

Anal. Found: C, 55.62; H, 5.65; N, 13.35.

NMR (DMSO-$d_6$): 1.87 (4,m), 3.40 (10 m), 4.00 (2,m), 6.61 (1,m), 7.25 (6,m), 7.85 (1,m).

IR: 750, 1120, 1315, 1450, 1540, 1640, 1710, 2590, 2940 cm$^{-1}$.

PROCEDURE 6

2-[4-[4(2-Methoxphenyl)-1-piperazinyl]-butyl]-1,2,4-triazolo[4,3-a]pyridin-3-(2H)-one Hydrochloride The method of Procedure 5 was followed employing 7.16 g. (0.022 mole) of 1-(2-methoxyphenyl)piperazine dihydrochloride, 5.83 g. (0.027 mole) of 1,4-dibromobutane, 14.92 g. (0.108 mole) of potassium carbonate, 4.3 g. (0.027 mole) of sodium 1,2,4-triazolo-[4,3-a]pyridin-3-one and 120 ml. of xylene. This time the oily residue from evaporation of the reaction mixture was purified by column chromatography using 220 g. of silica gel and chloroform containing 5% by volume of ethanol, and the 10% ethanol in chloroform for elution. the eluate was evaporated to yield 5.65 g. of oil which was converted to the hydrochloride salt by treatment with ethanolic HCl, recrystallized from ethanol, yield 3.85 g. (34.1%), m.p. 227°–229° (corr.).

Anal. Found: C, 60.38; H, 6.89; N, 16.67.

NMR (DMSO-$d_6$): 1.82 (4,m), 3.30 (10,m), 3.80 (3,s), 3.95 (2,m), 6.62 (1,m), 6.94 (4,m), 7.21 (2,m), 7.84 (1,m).

IR: 745, 1245, 1440, 1500, 1540, 1640, 1705, 1715, 2450, 2940 cm$^{-1}$.

By adaptation of Procedure 1 to various 2-chloro-3,4,5, or 6-lower alkyl substituted pyridine starting materials, and conversion of the resulting 5,6,7, or 8-lower alkyl-1,2,4-triazolo[4,3-a]-pyridin-3(2H)-ones according to the processes of Procedures 3 and 4, various substituted homologs of the product of Procedure 4 may be prepared as follows.

| Pyridine Starting Material | Formula I $R^2$ = 3-Cl |
|---|---|
| 2-Chloro-6-methylpyridine | $R^1$ = 5-$CH_3$ |
| 2-Chloro-6-ethylpyridine | $R^1$ = 5-$CH_2CH_3$ |
| 2-Chloro-6-(n-propyl)pyridine | $R^1$ = 5-(n-$C_3H_7$) |
| 2-Chloro-6-(tert.-butyl)pyridine | $R^1$ = 5-(tert.-butyl) |
| 2-Chloro-3-methylpyridine | $R^1$ = 8-$CH_3$ |
| 2-Chloro-4-methylpyridine | $R^1$ = 7-$CH_3$ |
| 2-Chloro-5-methylpyridine | $R^1$ = 6-$CH_3$ |

Similarly by substitution of other substituted or unsubstituted 1-phenylpiperazines for 1-(3-chlorophenyl)-piperazine in Procedure 4 various other $R^2$-substituted products of Formula I may be prepared as follows.

| Piperazine Starting Material | Formula I $R^1$ = H |
|---|---|
| 1-phenylpiperazine | $R^2$ = H |
| 1-(4-methylphenyl)piperazine | $R^2$ = 4-$CH_3$ |
| 1-(2-bromophenyl)piperazine | $R^2$ = 2-Br |
| 1-(4-fluorophenyl)piperazine | $R^2$ = 4-F |
| 1-(3-tert.-butylphenyl)piperazine | $R^2$ = 3-tert.-$C_4H_9$ |
| 1-(4-ethoxyphenyl)piperazine | $R^2$ = 4-$C_2H_5O$ |
| 1-[3-(1-methylethoxy)phenyl]piperazine | $R^2$ = 3-$OCH(CH_3)_2$ |

For the preparation of pharmaceutical compositions containing the compounds of Formula I in the form of dosage units for oral administration, the compound is mixed with a solid, pulverulent carrier such as lactose, sucrose, sorbitol, mannitol, potato starch, corn starch, amylopectin, cellulose derivatives, or gelatin, as well as with glidents such as magnesium stearate, calcium stearate, polyethylene glycol waxes or the like and compressed into tablets. The tablets may be used uncoated or coated by known techniques.

In the preparation of soft gelatin capsules comprised of a shell made of gelatin and glycerine or the like, the active ingredient is mixed with a vegetable oil and encapsulated in conventional manner. Hard gelatin capsules may contain granules of the active ingredient in combination with a solid, pulverulent carrier such as lactose, sucrose, sorbitol, mannitol, starch (such as e.g. potato starch, corn starch, or amylopectin), cellulose derivatives or gelatin.

Dose units for rectal administration may be prepared in the form of suppositories containing the compound in a mixture with a neutral fat base, or in the form of a gelatin-rectal capsule with a mixture of vegetable oil or paraffin oil.

Liquid preparations suitable for oral administration are suspensions, syrups and elixirs containing from about 0.2% by weight to about 20% by weight of the active ingredient.

A sutable injectible composition comprises an aqueous solution of a water soluble pharmaceutically acceptable salt adjusted to physiologically acceptable pH.

What is claimed is:

1. A triazolo[4,3-a]pyridin-3(2H)-one having the formula

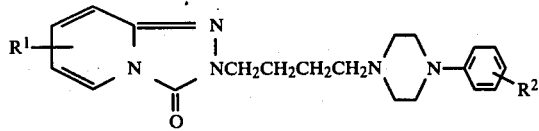

wherein $R^1$ is hydrogen or lower alkyl having 1 to 4 carbon atoms and located in the 5, 6, 7, or 8 positions of the triazolo[4,3-a]pyridin-3(2H)-one ring, and $R^2$ is located in the 2, 3, or 4 position of the phenyl ring and is trifluoromethyl and the pharmaceutically acceptable acid addition salts thereof.

2. The compound of claim 1 wherein $R^1$ is hydrogen and $R^2$ is trifluoromethyl.

3. The compound of claim 1, 2-[4[4-[3-)trifluoromethyl)-phenyl]-1-piperazinyl]butyl]-1,2,4-triazolo[4,3-a]pyridin-3(2H)-one.

4. The compound of claim 1, 2-[4[4-[3-(trifluoromethyl)-phenyl]-1-piperazinyl]butyl]-1,2,4-triazolo[4,3-a]pyridin-3(2H)-one hydrochloride.

5. The process for exerting an anti-psychotic effect which comprises administering orally or parenterally to a psychotic patient a non-toxic anti-psychotically effective dose of a compound having the formula

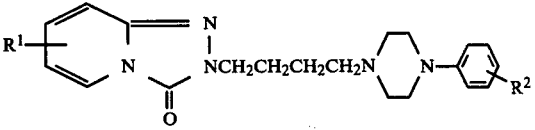

wherein $R^1$ is hydrogen or lower alkyl having 1 to 4 carbon atoms and located in the 5, 6, 7, or 8 positions of the triazolo[4,3-a]pyridin-3(2H)-one ring, and $R^2$ is hydrogen, or it is a substituent located in the 2, 3, or 4 position of the phenyl ring and selected from the group consisting of lower alkyl having 1 to 4 carbon atoms, lower alkoxy having 1 to 4 carbon atoms, halogen, or trifluoromethyl or a pharmaceutically acceptable acid addition salt thereof.

* * * * *